(12) United States Patent
Felipe et al.

(10) Patent No.: US 9,921,155 B2
(45) Date of Patent: Mar. 20, 2018

(54) METHODS OF DECREASING SCALE IN AQUEOUS SYSTEMS

(71) Applicant: BAKER HUGHES INCORPORATED, Houston, TX (US)

(72) Inventors: Mary Jane Felipe, Sugar Land, TX (US); Corina Sandu, Pearland, TX (US); David N. Fulmer, Missouri City, TX (US); Bing Bing Guo, Missouri City, TX (US)

(73) Assignee: Baker Hughes, a GE company, LLC, Houston, TX (US)

( * ) Notice: Subject to any disclaimer, the term of this patent is extended or adjusted under 35 U.S.C. 154(b) by 0 days.

(21) Appl. No.: 14/553,113

(22) Filed: Nov. 25, 2014

(65) Prior Publication Data

US 2016/0146734 A1    May 26, 2016

(51) Int. Cl.
*G01N 21/64* (2006.01)
*C02F 5/10* (2006.01)

(52) U.S. Cl.
CPC ............ *G01N 21/64* (2013.01); *C02F 5/10* (2013.01); *G01N 2201/06193* (2013.01)

(58) Field of Classification Search
CPC ........ C02F 5/14; C02F 2303/08; C02F 1/042; G01N 21/64; G01N 29/02
See application file for complete search history.

(56) References Cited

U.S. PATENT DOCUMENTS

| | | | |
|---|---|---|---|
| 3,890,228 A | 6/1975 | Hwa et al. | |
| 3,963,636 A | 6/1976 | Harris et al. | |
| 4,704,208 A * | 11/1987 | Bouet | C02F 5/12 210/698 |
| 5,135,661 A | 8/1992 | Patel | |
| 5,518,630 A | 5/1996 | Freese et al. | |
| 5,702,684 A * | 12/1997 | McCoy | A01N 61/00 210/745 |
| 5,948,268 A * | 9/1999 | Yamaguchi et al. | 210/701 |
| 6,344,531 B1 * | 2/2002 | Murray et al. | 526/268 |
| 8,741,151 B2 | 6/2014 | Hails et al. | |
| 2005/0242042 A1 | 11/2005 | Moriarty et al. | |
| 2008/0145549 A1 | 6/2008 | Kidambi | |
| 2008/0169243 A1 * | 7/2008 | Dave et al. | 210/699 |
| 2008/0295581 A1 | 12/2008 | Zhang et al. | |
| 2011/0214488 A1 * | 9/2011 | Rose | E21B 47/1015 73/61.71 |
| 2011/0253628 A1 * | 10/2011 | Blokker et al. | 210/638 |
| 2012/0032093 A1 * | 2/2012 | Moore et al. | 250/459.1 |

(Continued)

FOREIGN PATENT DOCUMENTS

| | | |
|---|---|---|
| EP | 624798 A1 | 11/1994 |
| EP | 365815 B2 | 8/1999 |
| WO | 2009111376 A1 | 9/2009 |

*Primary Examiner* — Marcus Taningco

(74) *Attorney, Agent, or Firm* — Mossman, Kumar & Tyler, P.C.

(57) ABSTRACT

Water-soluble polymers may be added to an aqueous system to inhibit or decrease scale deposition within the aqueous system. In a non-limiting embodiment, the water-soluble polymer(s) may be or include polymaleates, polyacrylates, copolymers thereof, and combinations thereof. The treated aqueous system may include a decreased amount of scale deposition as compared to an otherwise identical aqueous system absent the water-soluble polymer(s).

10 Claims, 2 Drawing Sheets

(56) References Cited

U.S. PATENT DOCUMENTS

2013/0043194 A1     2/2013   McNeel et al.
2013/0234063 A1     9/2013   Moore et al.
2015/0184069 A1*   7/2015   Nuutinen et al. .......... 250/459.1

* cited by examiner

METHODS OF DECREASING SCALE IN AQUEOUS SYSTEMS

TECHNICAL FIELD

The present invention relates to treated aqueous systems and methods for treating aqueous systems, and more specifically relates to adding water soluble polymers to the aqueous systems to decrease scale deposition.

BACKGROUND

The problems of scale deposition, corrosion, and attendant effects, such as pitting, have troubled water systems for years. For instance, scale tends to accumulate on internal walls of various water systems, and thereby materially lessening the operational efficiency of the system. In this manner, heat transfer functions of the particular system are severely impeded.

Water systems often have cooling water systems for cooling a water stream to a lower temperature and rejecting heat to the atmosphere. Cooling water towers may use the evaporation of water to remove process heat and cool the working fluid to near the wet-bulb air temperature, or may rely solely on air to cool the working fluid to near the dry-bulb air temperature in the case of a closed circuit dry cooling tower. Evaporation rates vary with changes in ambient wet bulb temperature, and thus contributes to water gains and losses during the cooling tower operation.

The formation of scales and/or deposits in industrial water systems may be inhibited by using water soluble polymers. However, using such water soluble polymers as anti-scalant or dispersant may be highly dependent on the concentration thereof. If too small of a concentration of the polymer is added to the water system, scaling and deposition will occur. On the other hand, if too large of a concentration of the polymer is added to the water system, the cost and performance efficiency of the water system may be adversely affected. With other methods of chemically treating aqueous systems, there is an optimal concentration of treatment chemicals to be maintained. Because of the desire to optimize the concentration of the polymer, determining the concentration of the polymers may be beneficial.

There are several methods of determining the concentration of water soluble polymers in aqueous water systems, such as but not limited to colorometric approaches (e.g. Hach polyacrylic acid method that uses thiocyanate chelation to detect calibration based on polyacrylic acid). However, these methods typically require a complicated, multi-step operation procedure and are difficult to carry out in the field. Turbidity method relies on the formation of insoluble compounds in determining the concentration of water soluble polymers. This method is lengthy and quite often susceptible to inaccuracies.

Since there are a lot of unknown variables and unknown volumetric changes inherent to cooling tower systems, there were also attempts to automate the precise addition of chemicals to cooling waters. Several technologies were patented by adding a fluorescent tag to cooling waters. Those technologies focused on measuring the amount of fluorescent tag to the system and correlate this amount to the concentration of the scale inhibitor. However, since a lot of factors affect the behavior of the fluorescent tag in the system (e.g. interaction of the fluorescent tag and the available scale inhibitor; interaction of the fluorescent tag to the scale formed, interaction of the fluorescent tag to the different water chemistry) that could interfere with the fluorescence reading, there is an ongoing need for the development of improved methods of monitoring and controlling the concentration of water treatment agents in cooling water systems.

Thus it would be desirable if methods and aqueous systems could be devised that decrease scale, yet enable a person or user to determine the actual concentration of these water soluble polymers in the chemical treatment of aqueous systems. It would also be desirable to have a simple method for detecting the water soluble polymers that has a decreased response to interferences, and where the method may be conducted on-site.

SUMMARY

There is provided, in one form, a treated aqueous system that may include an aqueous system and at least one water-soluble polymer, such as but not limited to polymaleates, polyacrylates, copolymers thereof, and combinations thereof. The treated aqueous system may have a decreased amount of scale deposition as compared to an otherwise identical aqueous system absent the water-soluble polymer(s).

There is provided in another non-limiting embodiment of the treated aqueous system where the system also includes a fluorometric device to detect at least one fluorescent property of the water-soluble polymer(s).

There is further provided, in another form, a method for decreasing scale in an aqueous system. The method may include circulating a water-based fluid through the aqueous system and decreasing scale deposition within the aqueous system as compared to an otherwise identical water-based fluid absent the water-based polymer. The aqueous system may include at least one water-based polymer, such as but not limited to, polymaleates, polyacrylates, copolymers thereof, and combinations thereof.

There is provided in another non-limiting embodiment of the method where the method also includes fluorescing the water-based polymer(s) and detecting a fluorescence of the water-based polymer(s) to determine a concentration of the water-based polymer(s) within the aqueous system.

DETAILED DESCRIPTION

Figure 1:
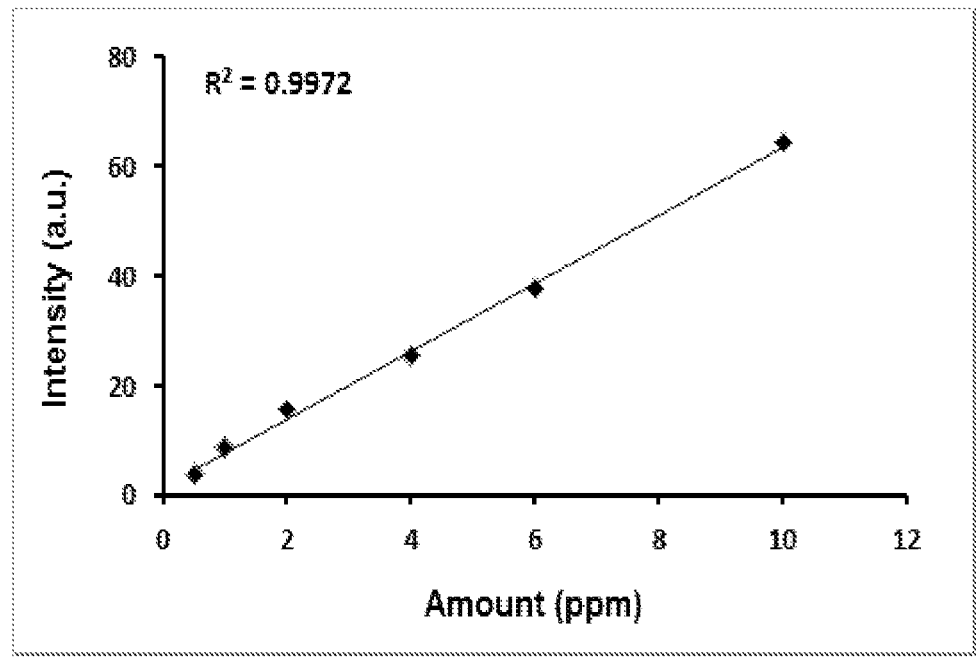
FIG. 1 is a graph illustrating the fluorescent intensity of the water-soluble polymers based on the concentration thereof within the samples.

It has been discovered that scale deposition within an aqueous system may be decreased or inhibited by adding a dispersant, such as, at least one water-soluble polymer into the aqueous system. The water-soluble polymer(s) may be or include polymaleates, polyacrylates, copolymers thereof, and combinations thereof. The treated aqueous system may have or include a decreased amount of scale deposition as compared to an otherwise identical aqueous system absent the water-soluble polymer(s). In a non-limiting embodiment, the water-soluble polymer(s) may be present in the water-based fluid in an amount ranging from about 200 ppb independently to about 20 ppm, or from about 500 ppb independently to about 12 ppm.

In a non-limiting embodiment, the water-soluble polymer(s) may have or include a fluorescent property to be detected by a fluorometric device, such as a fluorescence probe in a non-limiting embodiment. In a non-limiting embodiment, the fluorescent property may be intrinsic to the water-soluble polymer, or the fluorescent property may be added to the water-soluble polymer (e.g. a fluorescent tag added to the water-soluble polymer). The water-soluble polymers may fluoresce at a wavelength ranging from about 200 nm independently to about 400 nm, or from about 250 nm independently to about 350 nm in an alternative non-limiting embodiment. Non-limiting examples of the water-soluble polymer may be or include BELCLENE 200™ (a polymaleic acid—a calcium carbonate scale inhibitor) supplied by BWA Water Additives, Optidose™ (a polyacrylate copolymer—a calcium phosphate scale inhibitor) supplied by DOW Chemical Company, and combinations thereof.

In another non-limiting embodiment, the aqueous system may include at least one corrosion inhibitor, such as but not limited to triazoles, phosphinocarboxylates, phosphate-containing corrosion inhibitors, hydroxyl carboxylic acids, and combinations thereof. The phosphinocarboxylates may have a low-molecular weight, such as a molecular weight ranging from about 300 Daltons independently to about 20,000 Daltons, or from about 1,000 Daltons independently to about 10,000 Daltons in an alternative non-limiting embodiment.

In yet another non-limiting embodiment, the aqueous system may include at least one unit, such as but not limited to, a boiler, a cooling tower, a cooling water system, an evaporator, a gas scrubber, a kiln, a desalination unit, and combinations thereof.

In an alternative embodiment, a method for decreasing scale in an aqueous system may include circulating a water-based fluid through the aqueous system where the aqueous system includes at least one water-based polymer. The water-based polymer may be coated onto a component or unit within the aqueous system, or the water-based polymer may be added to a water-based fluid prior to circulating the water-based fluid through the aqueous system. The method may further include decreasing scale within the aqueous system.

In an alternative embodiment of the method, the method may include fluorescing a fluorescent property of the water-based polymer to be detected by the fluorometric device. A concentration of the fluorescence from the water-based polymer may be determined from the amount of fluorescence from the water-based polymer(s).

The water-soluble polymer(s) may suppress or reduce the amount of scale deposition within the aqueous system. That is, it is not necessary for scale deposition to be entirely prevented for the methods and aqueous systems discussed herein to be considered effective, although complete prevention is a desirable goal. Success is obtained if less scale deposition occurs using the water-soluble polymer(s) than in the absence of the water-soluble polymer(s). Alternatively, the methods and treated aqueous systems described are considered successful if there is at least a 50% decrease in scale deposition within the aqueous system.

The water-soluble polymer(s) and the corrosion inhibitor(s) may be added to the aqueous system at the same time as an additive, or the two components may be added at different times. The ratio of the water-soluble polymer(s) to the corrosion inhibitor may range from about 1:100 independently to about 1:0.1, or from about 1:25 independently to about 1:0.4. When added at the same time, the amount of the additive to be added to the aqueous system may range from about 4 ppm independently to about 500 ppm, or from about 4 ppm independently to about 300 ppm.

'Aqueous system' is defined herein to include an aqueous-based fluid and any components therein (e.g. pipes or conduits where the aqueous fluid may flow through or alongside) prior to adding the water-soluble polymer(s). The aqueous system may include an aqueous-based fluid flowing therethrough where the aqueous fluid may be or include, but is not limited to, water, brine, seawater, and combinations thereof. In a non-limiting embodiment, the aqueous based fluid may circulate through at least one unit of an aqueous system, such as but not limited to, a cooling tower, a cooling water system, a boiler, an evaporator, a gas scrubber, a kiln, a desalination unit, and combinations thereof. The cooling tower may be or include an open loop cooling tower, a closed loop cooling tower, and combinations thereof. 'Open loop' differs from 'closed loop' in that the 'open loop' system has recirculating water therethrough. The pH of the aqueous system may be greater than about 7, alternatively from about 7 to about 9, or from about 7.3 to about 8.5 in another non-limiting embodiment.

The aqueous system may be stable in the presence of chlorine-containing components, such as chloride salts. The chlorine-containing components may be present in the aqueous system prior to the addition of the water-soluble polymer(s). Alternatively, the chlorine-containing components may be added to the aqueous system at the same time or different time as the water-soluble polymer(s) in an amount ranging from about 1 ppm to about 1,000 ppm, alternatively from about 200 ppm independently to about 800 ppm, or an amount greater than about 500 ppm in another non-limiting embodiment.

The invention will be further described with respect to the following Examples, which are not meant to limit the invention, but rather to further illustrate the various embodiments.

EXAMPLES

Example 1

The intensity of a water-soluble polymer within each of six samples was measured. The six samples included the same components and had the same characteristics (e.g. pH, viscosity, etc.), except the amount of the water-soluble polymer varied for each sample. The base fluid for each sample was deionized (DI) water, and the water-soluble polymer was a fluorescent polymaleate. As noted in FIG. 1, an increased amount of the water-soluble polymer correlates to an increased intensity of fluorescence.

Example 2

Figure 2:
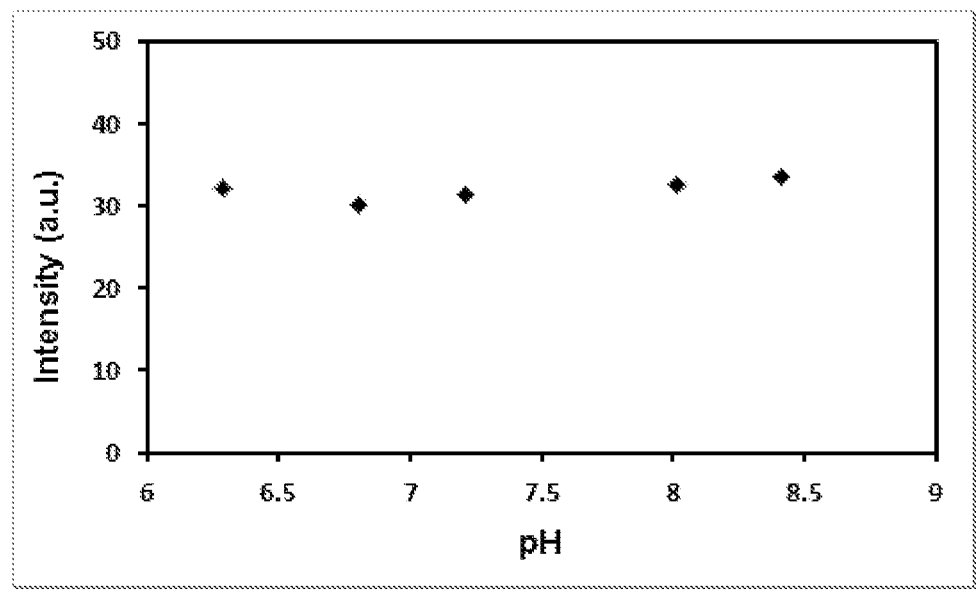
FIG. 2 is a graph illustrating the fluorescent intensity of the water-soluble polymers based on the pH of the samples.

The intensity of a water-soluble polymer was measured within each of five samples. The five samples included the same components and had the same characteristics (e.g. viscosity, water-soluble polymer concentration, etc.), except the pH varied for each sample. The concentration of the water-soluble polymer within each sample was 4 ppm. The base fluid for each sample was DI water, and the water-soluble polymer for each sample was a fluorescent polymaleate. As noted in FIG. 2, the intensity of the fluorescence from the water-soluble polymers within each sample remained about the same, even though the pH varied for each sample.

Example 3

Figure 3:
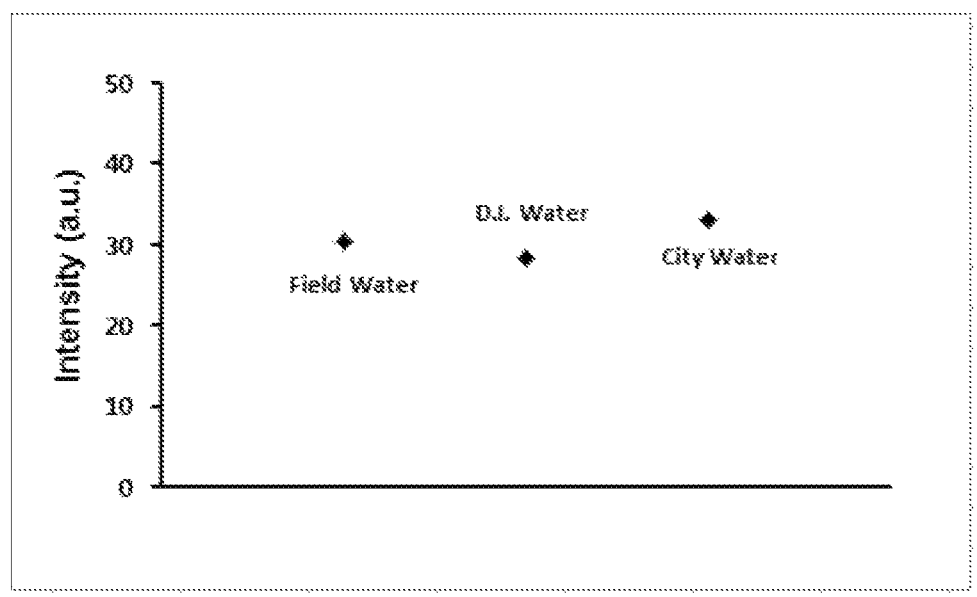
FIG. 3 is a graph illustrating the fluorescent intensity of the water-soluble polymers within samples having different types of water.

The intensity of a water-soluble polymer was measured within each of three samples. The three samples included the same components and had the same characteristics (e.g. viscosity, water-soluble polymer concentration, etc.), except the type of water-based fluid varied for each sample. A first sample included 'field water' taken from a Texas refinery as the base fluid. 'Field water' is defined herein as water taken from the Texas refinery and was unadulterated prior to using the field water as a base fluid for this set of testing. The second sample included deionized water. The third sample included city water taken from Sugar Land, Tex. as the base fluid. 'City water' is defined herein as water taken from a municipal water system of Sugarland, Tex. and was unadulterated prior to using the city water as a base fluid for this set of testing. The concentration of the water-soluble polymer for each sample was 4 ppm. The water-soluble polymer for each sample was a fluorescent-polymaleate. As noted in FIG. 3, the intensity of the fluorescence from the water-soluble polymers within each sample remained about the same, even though the type of water varied.

Example 4

Figure 4:
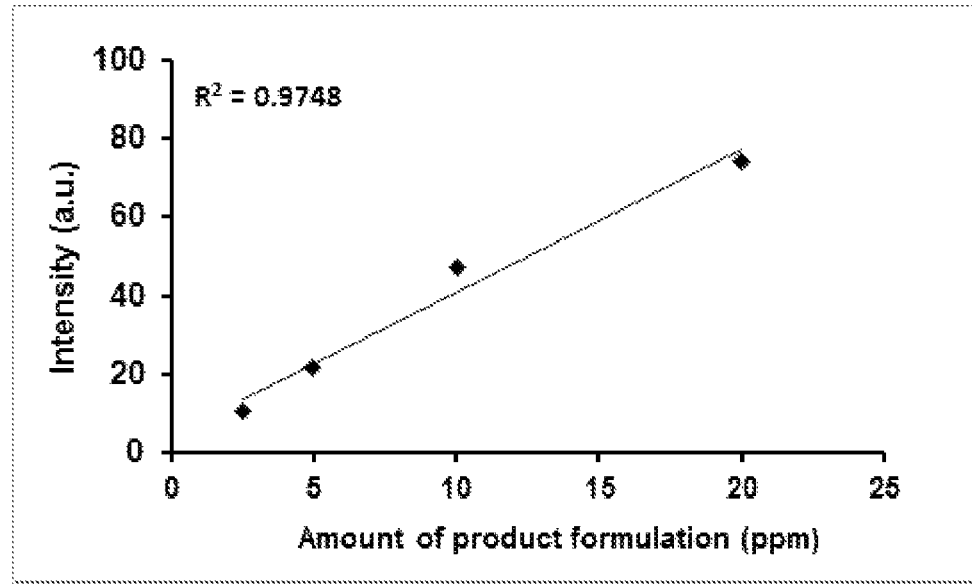
FIG. 4 is a graph illustrating the fluorescent intensity of the water-soluble polymers within samples where the water-soluble polymer varied within the total volume of each sample.

The intensity of a water-soluble polymer was measured within each of four samples. The four samples included the same components and had the same characteristics (e.g. viscosity, water-soluble polymer concentration, etc.), except the amount of product formulation varied for each sample. The concentration of the water-soluble polymer added to each sample varied. A first sample included the water-soluble polymer in an amount of 1.1 ppm; a second sample included the water-soluble polymer in an amount of 2.3 ppm; a third sample included the water-soluble polymer in an amount of 4.5 ppm; a fourth sample included the water-soluble polymer in an amount of 9.1 ppm. The base fluid for each sample was DI water, and the water-soluble polymer for each sample was a fluorescent-polymaleate. Each sample also included a corrosion inhibitor and a yellow corrosion inhibitor. As noted in FIG. 4, the intensity of the fluorescence from the water-soluble polymers within each sample increased as the amount of the water-soluble polymer increased within the total volume of each sample.

Example 5

Two sets of samples were measured to determine the ability of the water-soluble polymer to decrease scale. Each set included three samples where each sample included the same components and had the same characteristics (e.g. viscosity, pH, etc.), except the amount of the water-soluble polymer within each sample varied. The base fluid for the first set of samples was DI water and 500 ppm Ca(II). The base fluid for a second set of samples was DI water and 300 ppm Ca(II) in DI water. The water-soluble polymer added to each sample was a fluorescent-polymaleate.

As noted in TABLE 1, an increased amount of $CaCO_3$ scale inhibition was obtained for the first set of samples by increasing the amount of the water-soluble polymers within each sample. The amount of $CaSO_4$ inhibition for the second set of samples was relatively the same, regardless of the water-soluble polymer concentration.

TABLE 1

Polymer Concentration and Scale Inhibition Efficiency

| | Tagged Polymer Concentration | | |
|---|---|---|---|
| | 1 ppm | 2 ppm | 5 ppm |
| $CaCO_3$ Inhibition Efficiency (%) | 68.81 | 69.05 | 95.92 |
| $CaSO_4$ Inhibition Efficiency (%) | 100 | 104 | 100 |

In the foregoing specification, the invention has been described with reference to specific embodiments thereof, and has been described as effective in providing treated aqueous systems and methods for decreasing at least one characteristic within the aqueous system, such as but not limited to, corrosion, scale deposition and combinations thereof as compared to an otherwise identical aqueous system absent the water-soluble polymer(s). However, it will be evident that various modifications and changes can be made thereto without departing from the broader spirit or scope of the invention as set forth in the appended claims. Accordingly, the specification is to be regarded in an illustrative rather than a restrictive sense. For example, specific aqueous fluids, water-soluble polymers, hydroxycarboxylic acids, scale inhibitors, corrosion inhibitors, biocides, chlorine-containing components, and types of aqueous systems and/or aqueous system units falling within the claimed parameters, but not specifically identified or tried in a particular aqueous system or method, are expected to be within the scope of this invention.

The present invention may suitably comprise, consist or consist essentially of the elements disclosed and may be practiced in the absence of an element not disclosed. For instance, the treated aqueous system may consist of or consist essentially of an aqueous system and at least one water-soluble polymer, such as but not limited to polymaleates, polyacrylates, copolymers thereof, and combinations thereof; the treated aqueous system may have a decreased amount of scale deposition as compared to an otherwise identical aqueous system absent the at water-soluble polymer(s).

The method for decreasing scale in an aqueous system may consist of or consist essentially of circulating a water-based fluid through the aqueous system and decreasing scale deposition within the aqueous system as compared to an otherwise identical water-based fluid absent the water-based polymer; the aqueous system may include at least one water-based polymer, such as but not limited to, polymaleates, polyacrylates, copolymers thereof, and combinations thereof.

The words "comprising" and "comprises" as used throughout the claims, are to be interpreted to mean "including but not limited to" and "includes but not limited to", respectively.

What is claimed is:

1. A method for decreasing scale in an aqueous system while also detecting an amount of at least one water-soluble polymer in the aqueous system; wherein the method comprises:
    circulating a water-based fluid through the aqueous system; wherein the aqueous system comprises at least one corrosion inhibitor and at least one water-soluble polymer having an intrinsic fluorescent property; wherein the water-soluble polymer is selected from the group consisting of polymaleates, polyacrylates, copolymers thereof, and combinations thereof; and wherein the ratio of the at least one water soluble polymer to the at least one corrosion inhibitor is from about 1:100 to about 1:0.1;

fluorescing the at least one water-soluble polymer; and decreasing scale deposition within the aqueous system as compared to an otherwise identical water-soluble fluid absent the water-soluble polymer while also detecting a fluorescence of the at least one water-soluble polymer to determine a concentration of the at least one water-soluble polymer within the aqueous system.

2. The method of claim 1, wherein the at least one water-soluble polymer fluoresces at a wavelength ranging from about 200 nm to about 400 nm.

3. The method of claim 1, wherein the at least one water-soluble polymer is present in the water-based fluid in an amount ranging from about 200 ppb to about 20 ppm.

4. The method of claim 1, wherein the at least one corrosion inhibitor is selected from the group consisting of triazoles, phosphinocarboxylates, phosphate-containing corrosion inhibitors, hydroxycarboxylic acids, and combinations thereof.

5. The method of claim 1, wherein the aqueous system comprises at least one unit selected from the group consisting of a boiler, a cooling tower, a cooling water system, an evaporator, a gas scrubber, a kiln, a desalination unit, and combinations thereof.

6. The method of claim 4, wherein the at least one water-soluble polymer is a polymaleate that fluoresces at a wavelength ranging from about 200 nm to about 400 nm.

7. The method of claim 4, wherein the at least one water-soluble polymer is a polymaleate that is present in the water-based fluid in an amount ranging from about 200 ppb to about 20 ppm.

8. A method for decreasing scale in an aqueous system while also detecting an amount of at least one water-soluble polymaleate in the aqueous system; wherein the method comprises:

circulating a water-based fluid through the aqueous system; wherein the aqueous system comprises at least one corrosion inhibitor and at least one water-soluble polymaleate having an intrinsic fluorescent property; and wherein the ratio of the at least one water soluble polymaleate to the at least one corrosion inhibitor is from about 1:100 to about 1:0.1;

Fluorescing the at least one water-soluble polymaleate; and decreasing scale deposition within the aqueous system as compared to an otherwise identical water-soluble fluid absent the water-soluble polymaleate while also detecting a fluorescence of the at least one water-soluble polymaleate to determine a concentration of the at least one water-soluble polymaleate within the aqueous system;

wherein the at least one water-soluble polymaleate is present in the water-based fluid in an amount ranging from about 200 ppb to about 20 ppm and the at least one water-soluble polymaleate fluoresces at a wavelength ranging from about 200 nm to about 400 nm.

9. The method of claim 8, wherein the at least one corrosion inhibitor is selected from the group consisting of triazoles, phosphinocarboxylates, phosphate-containing corrosion inhibitors, hydroxycarboxylic acids, and combinations thereof.

10. The method of claim 8, wherein the aqueous system comprises at least one unit selected from the group consisting of a boiler, a cooling tower, a cooling water system, an evaporator, a gas scrubber, a kiln, a desalination unit, and combinations thereof.

* * * * *